(12) United States Patent
Luo

(10) Patent No.: US 8,012,565 B2
(45) Date of Patent: Sep. 6, 2011

(54) LYOCELL NONWOVEN WEBS

(75) Inventor: Mengkui Luo, Auburn, WA (US)

(73) Assignee: Weyerhaeuser NR Company, Federal Way, WA (US)

( * ) Notice: Subject to any disclaimer, the term of this patent is extended or adjusted under 35 U.S.C. 154(b) by 25 days.

(21) Appl. No.: 12/060,102

(22) Filed: Mar. 31, 2008

(65) Prior Publication Data

US 2009/0246447 A1    Oct. 1, 2009

(51) Int. Cl.
*B32B 3/00* (2006.01)
*B32B 3/02* (2006.01)
*B32B 5/26* (2006.01)

(52) U.S. Cl. ........ 428/156; 428/157; 442/381; 442/389; 442/392; 442/400; 442/409; 442/414

(58) Field of Classification Search ............... 442/381, 442/389, 392, 400, 409, 414; 428/156, 157, 428/78; 156/292, 306.3
See application file for complete search history.

(56) References Cited

U.S. PATENT DOCUMENTS

| 6,068,620 | A | 5/2000 | Chmieleski |
| 6,841,038 | B2 | 1/2005 | Horenziak et al. |
| 2003/0114814 | A1 | 6/2003 | Baker |
| 2006/0019571 | A1 | 1/2006 | Lange |
| 2006/0069375 | A1 | 3/2006 | Waksmundzki |
| 2007/0255243 | A1* | 11/2007 | Kaun et al. ............ 604/378 |
| 2008/0050565 | A1 | 2/2008 | Gross |

FOREIGN PATENT DOCUMENTS

WO    2007124522    11/2007

* cited by examiner

*Primary Examiner* — Norca L Torres Velazquez
(74) *Attorney, Agent, or Firm* — John M. Crawford

(57) ABSTRACT

Absorbent structures with nonwoven meltblown lyocell fiber webs are described which have excellent liquid distribution properties. The absorbent structures comprise at least two nonwoven meltblown lyocell fiber webs with superabsorbent polymer intermediate the two webs. Methods for making the structures are also described. The structures are particularly useful for use in disposable hygienic products.

18 Claims, 5 Drawing Sheets

LYOCELL NONWOVEN WEBS

FIELD

The present application relates to absorbent structures comprising nowoven meltblown lyocell fiber webs with superabsorbent polymers intermediate the webs. The absorbent structures can be used in disposable hygienic products.

BRIEF DESCRIPTION OF THE DRAWINGS

This invention is best understood from the following detailed description when read in connection with the accompanying drawings. It is emphasized that, according to common practice, various features of the drawings are not to scale. On the contrary, the dimensions of various features are arbitrarily expanded or reduced for clarity. Included in the drawings are the following Figures.

DESCRIPTION

Figure 1:
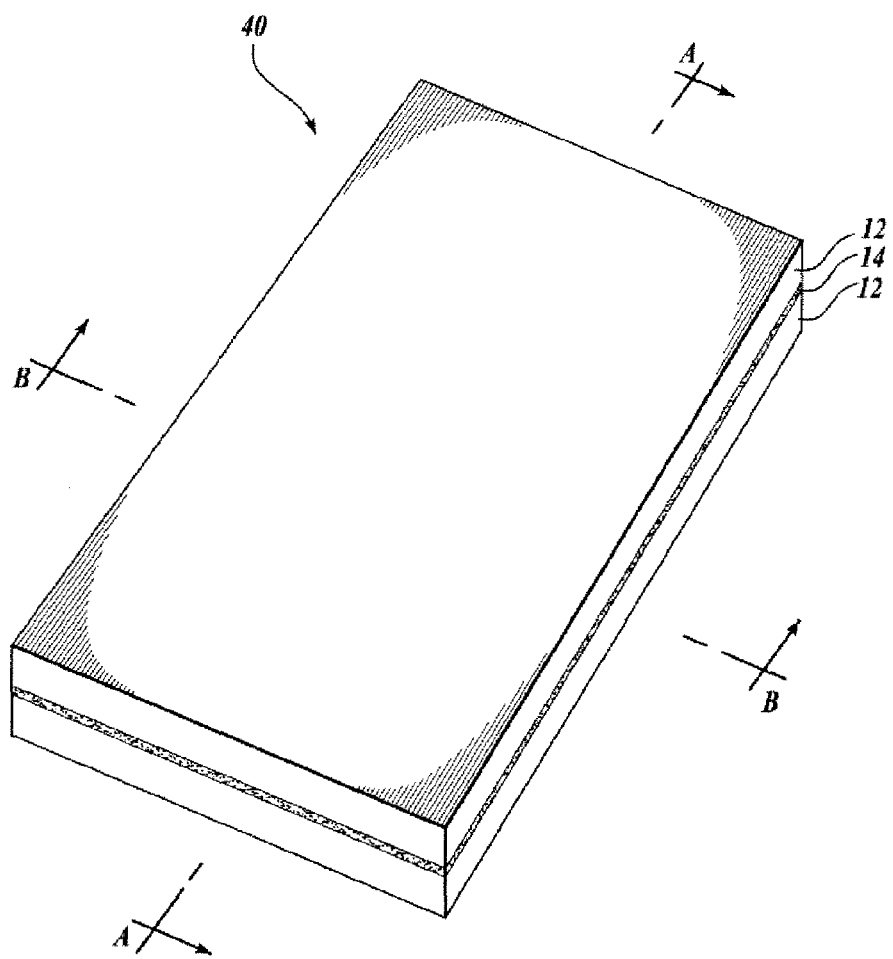
FIG. 1 is a plan view of an embodiment of a nonwoven meltblown lyocell fiber web structure.

Personal care absorbent products such as infant diapers, adult incontinence products, and feminine care products, can include liquid acquisition and/or distribution layers that serve to rapidly acquire and then distribute acquired liquid to a storage core for retention. To achieve rapid acquisition and distribution, these layers often include cellulosic fibers. These layers can include crosslinked cellulosic fibers to impart bulk and resilience to the layer, and wood pulp fibers to increase the wicking of liquid within the layer and to facilitate distribution of the liquid throughout the layer and ultimately to another layer, such as a storage layer, that is in liquid communication with the distribution layer. However, despite advances in these layers, the need exists for a more efficient liquid distribution within the storage core layer itself so as to make more efficient use of the material components and the entire absorbent structure. The present application seeks to fulfill these needs.

In one aspect the present application provides an absorbent structure comprising at least two nonwoven meltblown lyocell fiber webs with superabsorbent intermediate (i.e. between) the two nonwoven meltblown lyocell fiber webs which can be used as a storage core layer in a hygienic product.

In other aspects, the application provides personal care absorbent products that contain these absorbent structures and methods for making these.

Lyocell is made by dissolving cellulose in a mixture of N-methylmorpholine-N-oxide (NMMO) and water and extruding the solution into a regenerating bat, usually water. Lyocell is a generic term for a fiber composed of cellulose precipitated from an organic solution in which no substitution of hydroxyl groups takes place and no chemical intermediates are formed. Several manufacturers presently produce lyocell fibers, principally for use in the textile industry. For example, Lenzing, Ltd. presently manufactures and sells Tencel® fiber.

Lyocell fibers are particularly suitable for use in nonwoven applications because of their characteristic soft feel, water absorption, microdiameter size, biodegradability and the ability of these fibers to be combined in the spinning process to form either selfbonded or spunlaced webs. Fibers made from pulp with a high hemicellulose content are particularly suited for this application because of the added interfiber bonding attributed to hemicellulose.

Currently available lyocell fibers are produced from high quality wood pulps that have been extensively processed to remove non-cellulose components, especially hemicellulose. These highly processed pulps are referred to as dissolving grade or high a (high alpha) pulps, where the term a refers to the percentage of cellulose remaining after extraction with 17.5% caustic. Alpha cellulose can be determined by TAPPI 203. Thus, a high alpha pulp contains a high percentage of cellulose, and a correspondingly low percentage of other components, especially hemicellulose. The processing required to generate a high alpha pulp significantly adds to the cost of lyocell fibers and products manufactured therefrom. Typically, the cellulose for these high alpha pulps comes from both hardwoods and softwoods; softwoods generally have longer fibers than hardwoods.

In view of the expense of producing commercial dissolving grade pulps, it is desirable to have alternatives to conventional high alpha dissolving grade pulps as a lyocell raw material.

Low alpha (e.g., high yield) pulps can be used to make lyocell fibers. Preferably, the desired low alpha pulps will have a low copper number, a low lignin content and a desirably low transition metal content but broad molecular weight distribution.

Pulps which meet these requirements have been made and are described in U.S. Pat. No. 6,797,113, U.S. Pat. No. 6,686,093 and U.S. Pat. No. 6,706,876, the assignee of the present application. While high purity pulps are also suitable for use in the present application, low cost pulps such as Peach®, available from Weyerhaeuser, are suitable. These pulps provide the benefit of lower cost and better bonding for nonwoven textile applications because of their high hemicellulose content. Selected Peach® pulp properties are given in Table 1.

TABLE 1

| Peach ® Pulp Properties | |
|---|---|
| $S_{18}$, % | 11-14 |
| % Xylan | 7.05 |
| % Mannan | 6.10 |
| α-cellulose, % | 86 |
| IV, dl/g | 3.9-4.2 |
| Cu, number | <1.0 |
| g* | |
| Mn, Fe, Cu, ppm | <10 |
| Si, ppm | <52 |
| Extractives, % | <0.05 |

*per 100 g pulp

The term hemicellulose refers to a heterogeneous group of low molecular weight carbohydrate polymers that are associated with cellulose in wood. Hemicelluloses are amorphous, branched polymers, in contrast to cellulose which is a linear polymer. The principal, simple sugars that combine to form hemicelluloses are: D-glucose, D-xylose, D-mannose, L-arabinose, D-galactose, D-glucuronic acid and D-galacturonic acid.

Hemicellulose was measured in the fiber by the method described below for sugar analysis and represents the sum of the xylan and mannan content of the fiber.

Lyocell fibers prepared can be spun by various processes. In one embodiment the lyocell fiber is spun from cellulose dissolved in NMMO by the meltblown process. Where the term meltblown is used it will be understood that it refers to a process that is similar or analogous to the process used for the production of thermoplastic fibers, even though the cellulose is in solution and the spinning temperature is only moderately elevated. In another embodiment the fiber is spun by the centrifugal spinning process, in another embodiment the fiber is spun by the dry-jet-wet process and in yet another embodiment the fiber is spun by the spun bonding process. Fibers formed by the meltblown process can be continuous or discontinuous depending on air velocity, air pressure, air temperature, viscosity of the solution, D.P. of the cellulose and combinations thereof; in the continuous process the fibers are taken up by a reel and optionally stretched. In one embodiment for making a nonwoven web the fibers are contacted with a non solvent such as water (or water NMMO mixture) by spraying, subsequently taken up on a moving foraminous support, washed and dried. The fibers formed by this method can be in a bonded nonwoven web depending on the extent of coagulation or if it is spunlaced. Spunlacing involves impingement with a water jet. A somewhat similar process is called "spunbonding" where the fiber is extruded into a tube and stretched by an air flow through the tube caused by a vacuum at the distal end. In general, spunbonded synthetic fibers are longer than meltblown synthetic fibers which usually come in discrete shorter lengths. In the present application the fibers are continuous. Another process, termed "centrifugal spinning", differs in that the polymer is expelled from apertures in the sidewalls of a rapidly spinning drum. The fibers are stretched somewhat by air resistance as the drum rotates. However, there is not usually a strong air stream present as in meltblowing. The other technique is dry jet/wet. In this process the filaments exiting the spinneret orifices pass through an air gap before being submerged and coagulated in a liquid bath. All four processes may be used to make nonwoven fabrics of the present application.

In one embodiment the fibers are made from a pulp with greater than three percent by weight hemicellulose. In another embodiment the fibers are made from a pulp with greater than eight percent by weight hemicellulose. In yet another embodiment the fibers are made from a pulp with greater than twelve percent by weight hemicellulose.

In one embodiment the meltblown cellulose fibers contain from about 4.0 to about 18% by weight hemicellulose as defined by the sum of the xylan and mannan content of the fibers. In another embodiment the fibers contains from about 7 to about 14% by weight hemicellulose and in yet another embodiment the fibers contain from about 9% to about 12 percent by weight hemicellulose.

The present application provides absorbent structures of nonwoven meltblown lyocell fiber webs that distribute and transfer liquid effectively throughout the entire structure. The nonwoven webs comprise meltblown lyocell fibers of continuous length. In one embodiment the meltblown lyocell fibers in the web have a diameter of from 3 to 20 microns. In another embodiment the meltblown lyocell fibers in the web have a fiber diameter of from 5 to 15 microns and in yet another embodiment to diameter is from 7 to 10 microns.

The basis weights of the individual nonwoven meltblown lyocell fiber webs in the absorbent structure can be the same or they can be different. In one embodiment the basis weight of an individual web ranges from about 5 $g/m^2$ to about 150 $g/m^2$. In another embodiment the basis weight ranges from about 15 $g/m^2$ to about 100 $g/m^2$. Other embodiments are from about 20 $g/m^2$ to about 50 $g/m^2$ and from about 25 $g/m^2$ to about 40 $g/m^2$. Combinations of different basis weights of the nonwoven meltblown lyocell fiber webs can be used.

In one embodiment the absorbent structure has at least two nonwoven meltblown lyocell fiber webs in which the lower surface of one web is in intimate contact with the upper surface of the other web. A superabsorbent polymer is intermediate the two nonwoven meltblown lyocell fiber webs. As used herein, a SAP or "superabsorbent particles" or "superabsorbent polymer" refers to a polymer that is capable of absorbing large quantities of fluid by swelling and fanning a hydrated gel (i.e., a hydrogel). In addition to absorbing large quantities of fluids, superabsorbent polymers can also retain significant amounts of bodily fluids under moderate pressure. Superabsorbent polymers are available commercially, for example, BASF Hi-Sorb 8600 from BASF, Ludwigshafen, Germany. Other superabsorbent polymer are marketed under the trademarks SANWET (supplied by Sanyo Kasei Kogyo Kabushiki Kaisha), and Drytech, supplied by Degussa AG, Dusseldorf, Germany. Other superabsorbent polymer are described in U.S. Pat. No. 4,160,059; U.S. Pat. No. 4,676,784; U.S. Pat. No. 4,673,402; U.S. Pat. No. 5,002,814; U.S. Pat. No. 5,057,166; U.S. Pat. No. 4,102,340; and U.S. Pat. No. 4,818,598. Products such as diapers that incorporate superabsorbent polymer are described in U.S. Pat. No. 3,699,103 and U.S. Pat. No. 3,670,731. Biodegradeable superabsorbents such as LYSORB® 218 from ADM, Decatur, Ill., a starch based superabsorbent can also be used in the present application.

In absorbent structures with two or more dried nonwoven meltblown lyocell fiber webs and having superabsorbent polymer intermediate at least two of the webs, the perimeter of the structure can be compressed such that the pressed edge area has a lower thickness and higher density than the unpressed adjacent area. Bonding agents can be used to bond the webs in the pressed areas. Alternatively, the entire structure can be pressed to a lower thickness and a higher density than the original thickness and density of the original structure. Suitable bonding agents at the interface of the edges of the webs or the entire web include application of a water spray, a solution of carboxymethyl cellulose available from Hercules Wilmington Del. as Aqualon. Adhesives may also be used with preference to biodegradeable adhesives such as Polylactic, Acid (PLA) or Ingeo from NatureWorks LLC, Minnetonka Mn, starch based adhesives from National Starch and Chemical Company, Bridgewater, N.J. and soybean based adhesives from Biobased Technologies. Rogers, Ak. Polyvinyl alcohol may also be used. The perimeter of the absorbent structure can also be embossed to obtain bonding.

Never dried nonwoven meltblown lyocell fiber webs are also suitable for manufacture of absorbent structures of the present application. In an exemplary method, a never dried nonwoven meltblown lyocell fiber web is laid down edge, superabsorbent polymer uniformly dispersed over the surface of the web within approximately 5 mm of each and then a second never dried nonwoven meltblown lyocell fiber web is laid down over the first web. The combined web structure is then pressed and dried under restraint. Alternately, the edges of the structure may be pressed before drying. The same method is used with dried webs except that a bonding agent is used before pressing the entire structure or the edges.

Absorbent structures with at least two nonwoven webs can be embossed and, as a consequence, the superabsorbent intermediate the two webs can reside in pockets within the absorbent structure. This feature allows expansion of the superabsorbent upon wetting.

Depending on the absorbency needed, absorbent structures with multiple nonwoven meltblown lyocell webs with the same or different basis weights with superabsorbent intermediate any one or more adjacent webs can be used.

Figure 2:
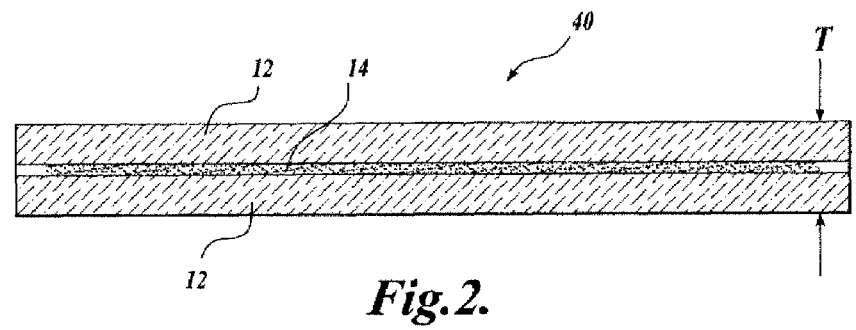
FIG. 2 is a cross section view of the nonwoven meltblown lyocell fiber web structure in FIG. 1 viewed along section line A-A.
Figure 2A:
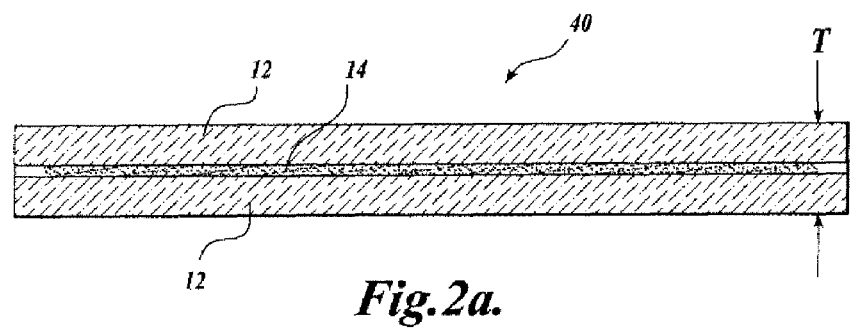
FIG. 2a is a cross section of the nonwoven meltblown lyocell fiber web structure in FIG. 1 viewed along section line B-B.
Figure 3:
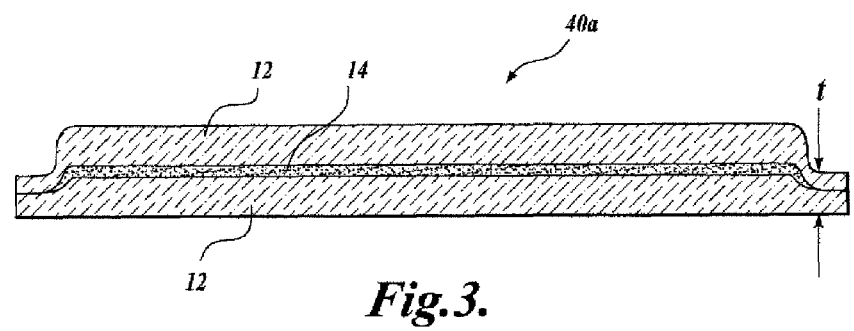
FIG. 3 is a cross section of the nonwoven meltblown lyocell fiber web structure of FIG. 1-2a compressed along the edges as depicted in FIG. 8 described below.
Figure 4:
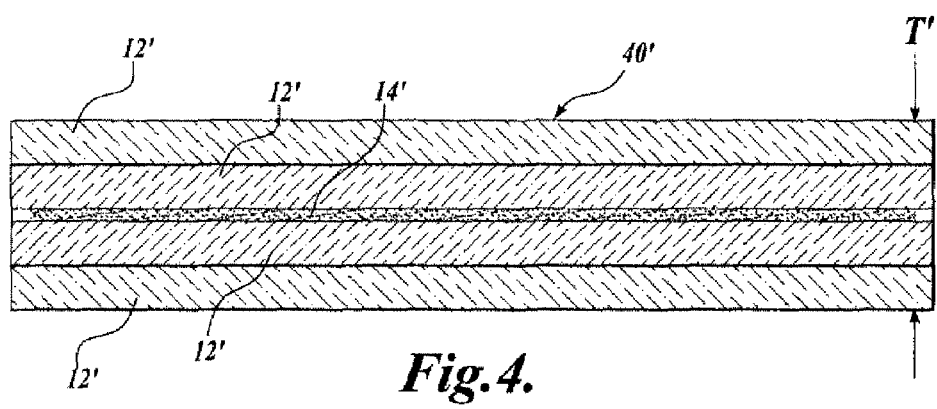
FIG. 4 is an additional embodiment of the nonwoven meltblown lyocell fiber web structure.
Figure 5:
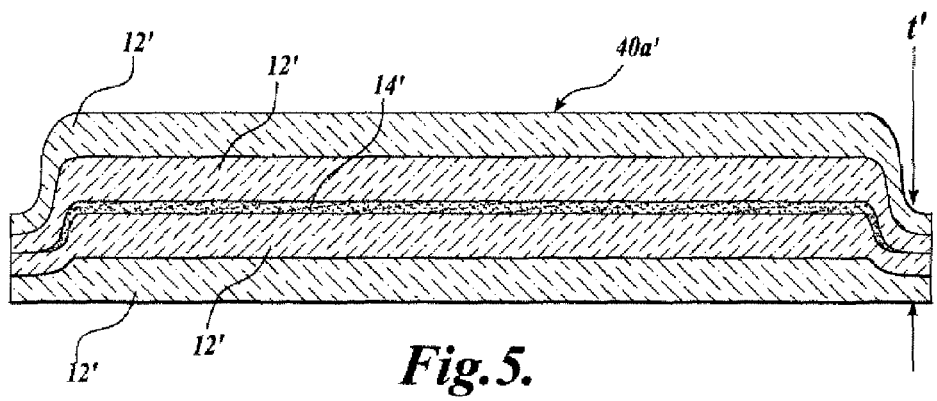
FIG. 5 is the nonwoven meltblown lyocell fiber web structure in FIG. 4 compressed along the edges.
Figure 6:
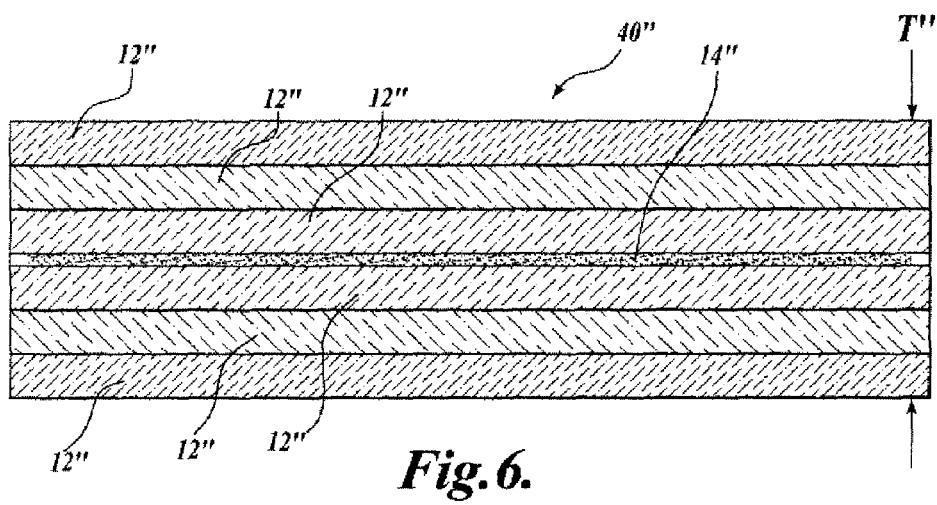
FIG. 6 is yet another embodiment of the nonwoven meltblown lyocell fiber structure.
Figure 7:
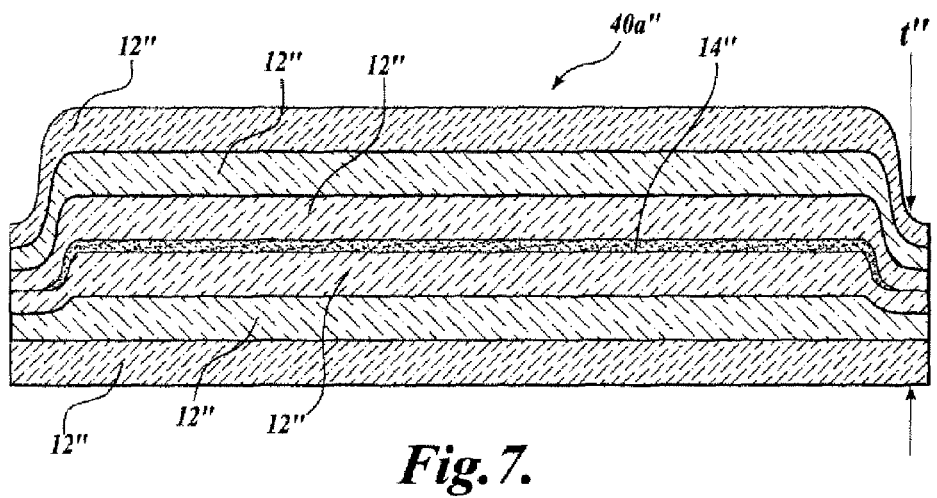
FIG. 7 is the nonwoven meltblown lyocell fiber web structure of FIG. 6 compressed along the edges.
Figure 8:
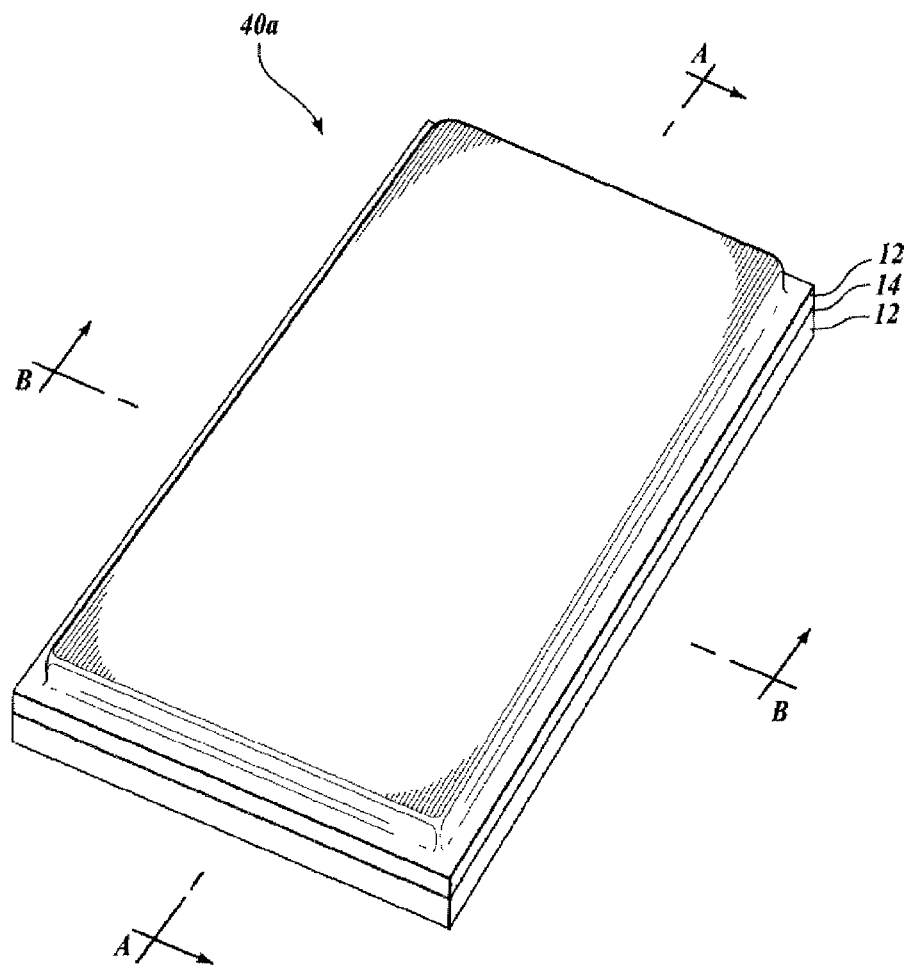
FIG. 8 is a plan view of a nonwoven meltblown lyocell fiber web structure showing the compressed edges.

Referring to the figures, it is understood that embodiments of the figures are only exemplary and are not meant to limit the scope of the claims. In all figures, like numbers refer to like components. Numbers indicated in prime represent like material. FIG. 1 is a plan view of an embodiment of an absorbent structure with two nonwoven meltblown lyocell webs. 40 is the nonwoven web structure, 12a nonwoven web and 14 is superabsorbent. The nonwoven webs can be of the same or different basis weight. FIGS. 2 and 2a are cross section views of the two nonwoven meltblown lyocell webs in FIG. 1 along the A-A and B-B axis, respectively. T is the initial thickness of the web structure. FIG. 3 is a cross section of the nonwoven meltblown web structure of FIG. 1 compressed along the edges to a thickness t and as depicted in FIG. 8. It is understood that the overall web structure can be pressed from the initial thickness, T, to the same final thickness t as the edges. FIG. 4, web structure 40', is an additional embodiment of the nonwoven meltblown lyocell web structure depicting two webs 12' and superabsorbent 14', with an initial thickness T' of the web structure. FIG. 5, web structure 40a', is the nonwoven meltblown lyocell web structure of FIG. 4 compressed along the edges to a final thickness t'. The nonwoven meltblown lyocell webs may be of the same or different basis weights. Also, superabsorbent polymer may be intermediate any one or more of the webs. FIG. 6, web structure 40" is yet another embodiment of the nonwoven meltblown lyocell web structure depicting webs 12" with superabsorbent 14" intermediate two adjacent webs and the web structure thickness of T". FIG. 7, web structure 40a" shows the web of FIG. 6 compressed at the edges to a final thickness t". It is understood that, as before, the webs can be of the same or different basis weight and that superabsorbent polymer can be intermediate any two or more webs. FIG. 8 is a plan view of a nonwoven meltblown lyocell fiber web structure 40a showing the compressed edges. 12 represents the nonwoven lyocell web and 14 represents the superabsorbent.

Nonwoven Meltblown Lyocell Web Preparation

Sample 52-5 was prepared from 8.0% Peach® at 0.3 g/h/m at 110° C. using a 600 hole/60 cm wide nozzle. The basis weight was 40 g/m², the fiber diameter was 9.8 micron. The meltblown air temperature was 130° C. and the air pressure 1.0 psi (0.703 kg/cm². Water was sprayed on the dope strands between the nozzle and the conveyor belt and the fibrous web collected on a moving conveyor belt. The deposited web was washed by spraying water using several beams of spray nozzles. The water was collected in a tripartite tank for counter current washing. The last washing step, (third step), used fresh softened water which was collected for the washing stage before the last one or for the second washing stage. The wash water collected from the second wash stage was used for the first stage wash. Water from the first section under the nozzle was pumped to solvent recovery. The NMMO concentration in the wash water of the first bath was approximately 2.5 to 4 percent. After the last washing the web was passed through a squeeze roll to remove water to a solid content of 15 to 35 percent and then collected on a winder. The hemicellulose content of the fiber in the web was 5.1% xylan and 4.3% mannan.

Sample 59-2 was prepared from 8.0% Peach at 0.25 g/h/m at 114° C. using 600 hole/60 cm wide nozzle. The basis weight was 36 g/m², the diameter 9.2 micron. The meltblown air temperature was 130° C. and the air pressure 1.0 psi (0.703 kg/m²). Water was sprayed on the dope strands between the nozzle and the conveyor belt and the fibers collected on a moving conveyor belt. The deposited web was washed again by spraying water using several beams of spray nozzles. The water was collected in a tripartite tank for counter current washing. The last washing step, (third washing), used fresh softened water which was collected for the washing stage before the last one or for the second washing stage. The wash water collected from the second wash stage was used for the first stage wash. Water from the first section under the nozzle was pumped to solvent recovery. The NMMO concentration in the wash water of the first bath was approximately 2.5 to 4 percent. After the last washing the web was passed through a squeeze roll to remove water to a solid content of 15 to 35 percent and then collected on a winder. The nonwoven web was dried on a 1 meter belt drier at a temperature of from 95° C.-110° C. at a speed of 2 to 5 m/min. Alternatively a screen drum drier was used. The drying temperature was from 100° C.-110° C. at a speed of 6 to 10 m/min. Air circulation of the blower was 80%. The hemicellulose content of the fiber in the web was 5.2% xylan and 4.2% mannan.

Sample 46-4 was prepared from 8.0% Peach at 0.25 g/h/m at 114° C. using a 600 hole/60 cm wide nozzle. The basis weight was 45 g/m², the diameter, 9.2 micron. The meltblown air temperature was 130° C. and the air pressure 1.0 psi (0.703 kg/cm²). Water was sprayed on the dope strands between the nozzle and the conveyor belt and the fibers collected on a moving conveyor belt. The deposited web was washed again by spraying water using several beams spray nozzles. The water was collected in a tripartite tank for counter current washing. The last washing step, (third washing), used fresh softened water which was collected for the washing stage before the last one or for the second washing stage. The wash water collected from the second wash stage was used for the first stage wash. Water from the first section under the nozzle was pumped to solvent recovery. The NMMO concentration in the wash water of the first bath was approximately 2.5 to 4 percent. After the last washing the web was passed through a squeeze roll to remove water to a solid content of 15 to 35 percent and then collected on a winder. The collected web, in the wet state, was optionally spunlaced and dried by the screen belt drier method or the screen drum method described above. Spunlacing was performed on Aqua Jet equipment from the Fleissner Company. The unit was equipped with one drum with three beams, each beam having 40 nozzles/inch and each nozzle having a diameter of 120μ. The water pressure was 3 bar and the initial water temperature was about 20° C. which increased with running to 30° C. to 40° C. The vacuum was 0.8 bar and the unit was run at a speed of 5 m/min. Drying was conducted either on a belt drier or a screen drum drier as previously described. The hemicellulose content of the fiber in the web was 5.0% xylan and 4.2% mannan.

Sugar Analysis

This method is applicable for the preparation and analysis of pulp and wood samples for the determination of the amounts of the following pulp sugars: fucose, arabinose, galactose, rhamnose, glucose, xylose and mannose using high performance anion exchange chromatography and pulsed amperometric detection (HPAEC/PAD).

SUMMARY OF METHOD

Polymers of pulp sugars are converted to monomers by hydrolysis using sulfuric acid. Samples are ground, weighed, hydrolyzed, diluted to 200-mL final volume, filtered, diluted again (1.0 mL+8.0 mL $H_2O$) in preparation for analysis by HPAEC/PAD.

Sampling, Sample Handling and Preservation

Wet samples are air-dried or oven-dried at 25±5° C.

Equipment Required

Autoclave, Market Forge, Model # STM-E, Serial # C-1808

100×10 mL Polyvials, septa, caps, Dionex Cat # 55058

Gyrotory Water-Bath Shaker, Model G76 or some equivalent.

Balance capable of weighing to ±0.01 mg, such as Mettler HL52 Analytical Balance.

Intermediate Thomas-Wiley Laboratory Mill, 40 mesh screen.

NAC 1506 vacuum oven or equivalent.

0.45-µ GHP filters, Gelman type A/E, (4.7-cm glass fiber filter discs, without organic binder)

Heavy-walled test tubes with pouring lip, 2.5×20 cm.

Comply SteriGage Steam Chemical Integrator

GP 50 Dionex metal-free gradient pump with four solvent inlets

Dionex ED 40 pulsed amperometric detector with gold working electrode and solid state reference electrode Dionex autosampler AS 50 with a thermal compartment containing the columns, the ED 40 cell and the injector loop Dionex PC10 Pneumatic Solvent Addition apparatus with 1-L plastic bottle 3 2-L Dionex polyethylene solvent bottles with solvent outlet and helium gas inlet caps CarboPac PAI (Dionex P/N 035391) ion-exchange column, 4 mm×250 mm CarboPac PAI guard column (Dionex P/N 043096), 4 mm×50 mm Millipore solvent filtration apparatus with Type HA 0.45 u filters or equivalent Reagents Required All references to $H_2O$ is Millipore $H_2O$ 72% Sulfuric Acid Solution (H2SO4)—Transfer 183 mL of water into a 2-L Erlenmeyer flask. Pack the flask in ice in a Rubbermaid tub in a hood and allow the flask to cool.

Slowly and cautiously pour, with swirling, 470 mL of 96.6% $H_2SO_4$ into the flask. Allow solution to cool. Carefully transfer into the bottle holding 5-mL dispenser. Set dispenser for 1 mL.

JT Baker 50% sodium hydroxide solution, Cat. No. Baker 3727-01, [1310-73-2]

Dionex sodium acetate, anhydrous (82.0±0.5 grams/1 L $H_2O$), Cat. No. 59326, [127-09-3].

Standards

Internal Standards

Fucose is used for the kraft and dissolving pulp samples. 2-Deoxy-D-glucose is used for the wood pulp samples.

Fucose, internal standard. 12.00±0.005 g of Fucose, Sigma Cat. No. F 2252, [2438-80-4], is dissolved in 200.0 mL $H_2O$ giving a concentration of 60.00±0.005 mg/mL. This standard is stored in the refrigerator.

2-Deoxy-D-glucose, internal standard. 12.00±0.005 g of 2-Deoxy-D-glucose, Fluka Cat. No. 32948 g [101-77-9] is dissolved in 200.0 mL $H_2O$ giving a concentration of 60.00±0.005 mg/mL. This standard is stored in the refrigerator.

Kraft Pulp Stock Standard Solution

| KRAFT PULP SUGAR STANDARD CONCENTRATIONS | | | |
|---|---|---|---|
| Sugar | Manufacturer | Purity | g/200 mL |
| Arabinose | Sigma | 99% | 0.070 |
| Galactose | Sigma | 99% | 0.060 |
| Glucose | Sigma | 99% | 4.800 |
| Xylose | Sigma | 99% | 0.640 |
| Mannose | Sigma | 99% | 0.560 |

Kraft Pulp Working Solution

Weigh each sugar separately to 4 significant digits and transfer to the same 200-mL volumetric flask. Dissolve sugars in a small amount of water. Take to volume with water, mix well, and transfer contents to two clean, 4-oz. amber bottles. Label and store in the refrigerator. Make working standards as in the following table.

| PULP SUGAR STANDARD CONCENTRATIONS FOR KRAFT PULPS | | | | | | |
|---|---|---|---|---|---|---|
| Fucose Sugar | mg/mL | mL/200 mL 0.70 ug/mL | mL/200 mL 1.40 ug/mL | mL/200 mL 2.10 ug/mL | mL/200 mL 2.80 ug/mL | mL/200 mL 3.50 ug/mL |
| Fucose | 60.00 | 300.00 | 300.00 | 300.00 | 300.00 | 300.00 |
| Arabinose | 0.36 | 1.2 | 2.5 | 3.8 | 5.00 | 6.508 |
| Galactose | 0.30 | 1.1 | 2.2 | 3.30 | 4.40 | 5.555 |
| Glucose | 24.0 | 84 | 168.0 | 252.0 | 336.0 | 420.7 |
| Xylose | 3.20 | 11 | 22.0 | 33.80 | 45.00 | 56.05 |
| Mannose | 2.80 | 9.80 | 19.0 | 29.0 | 39.0 | 49.07 |

Dissolving Pulp Stock Standard Solution

| DISSOLVING PULP SUGAR STANDARD CONCENTRATIONS | | | |
|---|---|---|---|
| Sugar | Manufacturer | Purity | g/100 mL |
| Glucose | Sigma | 99% | 6.40 |
| Xylose | Sigma | 99% | 0.120 |
| Mannose | Sigma | 99% | 0.080 |

Dissolving Pulp Working Solution

Weigh each sugar separately to 4 significant digits and transfer to the same 200-mL volumetric flask. Dissolve sugars in a small amount of water. Take to volume with water, mix well, and transfer contents to two clean, 4-oz. amber bottles. Label and store in the refrigerator. Make working standards as in the following table.

| PULP SUGAR STANDARD CONCENTRATIONS FOR DISSOLVING PULPS | | | | | | |
|---|---|---|---|---|---|---|
| Fucose Sugar | mg/mL | mL/200 mL 0.70 ug/mL | mL/200 mL 1.40 ug/mL | mL/200 mL 2.10 ug/mL | mL/200 mL 2.80 ug/mL | mL/200 mL 3.50 ug/mL |
| Fucose | 60.00 | 300.00 | 300.00 | 300.00 | 300.00 | 300.00 |
| Glucose | 64.64 | 226.24 | 452.48 | 678.72 | 904.96 | 1131.20 |
| Xylose | 1.266 | 4.43 | 8.86 | 13.29 | 17.72 | 22.16 |
| Mannose | 0.8070 | 2.82 | 5.65 | 8.47 | 11.30 | 14.12 |

Wood Pulp Stock Standard Solution

| WOOD PULP SUGAR STANDARD CONCENTRATIONS | | | |
|---|---|---|---|
| Sugar | Manufacturer | Purity | g/200 mL |
| Fucose | Sigma | 99% | 12.00 |
| Rhamnose | Sigma | 99% | 0.0701 |

Dispense 1 mL of the fucose solution into a 200-mL flask and bring to final volume.

Final concentration will be 0.3 mg/mL.

Wood Pulp Working Solution

Use the Kraft Pulp Stock solution and the fucose and rhamnose stock solutions. Make working standards as in the following table.

| PULP SUGAR STANDARD CONCENTRATIONS FOR KRAFT PULPS | | | | | | |
|---|---|---|---|---|---|---|
| 2-Deoxy-D-glucose Sugar | mg/mL | mL/200 mL 0.70 ug/mL | mL/200 mL 1.40 ug/mL | mL/200 mL 2.10 ug/mL | mL/200 mL 2.80 ug/mL | mL/200 mL 3.50 ug/mL |
| 2-DG | 60.00 | 300.00 | 300.00 | 300.00 | 300.00 | 300.00 |
| Fucose | 0.300 | 1.05 | 2.10 | 3.15 | 4.20 | 6.50 |
| Arabinose | 0.36 | 1.2 | 2.5 | 3.8 | 5.00 | 6.508 |
| Galactose | 0.30 | 1.1 | 2.2 | 3.30 | 4.40 | 5.555 |
| Rhamnose | 0.3500 | 1.225 | 2.450 | 3.675 | 4.900 | 6.125 |
| Glucose | 24.00 | 84 | 168.0 | 252.0 | 336.0 | 420.7 |
| Xylose | 3.20 | 11 | 22.0 | 33.80 | 45.00 | 56.05 |
| Mannose | 2.80 | 9.80 | 19.0 | 29.0 | 39.0 | 49.07 |

Procedure

Sample Preparation

Grind 0.2±05 g sample with Wiley Mill 40 Mesh screen size. Transfer ~200 mg of sample into 40-mL Teflon container and cap. Dry overnight in the vacuum oven at 50° C. Add 1.0 mL 72% $H_2SO_4$ to test tube with the Brinkman dispenser. Stir and crush with the rounded end of a glass or Teflon stirring rod for one minute. Turn on heat for Gyratory Water-Bath Shaker. The settings are as follows:

Heat: High

Control Thermostat: 7° C.

Safety thermostat: 25° C.

Speed: Off

Shaker: Off

Place the test tube rack in gyratory water-bath shaker. Stir each sample 3 times, once between 20-40 min, again between 40-60 min, and again between 60-80 min. Remove the sample after 90 min. Dispense 1.00 mL of internal standard (Fucose) into Kraft samples. Tightly cover samples and standard flasks with aluminum foil to be sure that the foil does not come off in the autoclave.

Place a Comply SteriGage Steam Chemical Integrator on the rack in the autoclave.

Autoclave for 60 minutes at a pressure of 14-16 psi (95-105 kPa) and temperature >260° F. (127° C.).

Remove the samples from the autoclave. Cool the samples. Transfer samples to the 200-mL volumetric flasks. Add 2-deoxy-D-glucose to wood samples. Bring the flask to final volume with water.

For Kraft and Dissolving pulp samples:

Filter an aliquot of the sample through GHP 0.45µ filter into a 16-mL amber vial.

For Wood pulp samples:

Allow particulates to settle. Draw off approximately 10 mL of sample from the top, trying not to disturb particles and filter the aliquot of the sample through GHP 0.45µ filter into a 16-mL amber vial. Transfer the label from the volumetric flask to the vial. Add 1.00 mL aliquot of the filtered sample with to 8.0 mL of water in the Dionex vial.

Samples are run on the Dionex AS/500 system. See Chromatography procedure below.

Chromatography Procedure

Solvent Preparation

Solvent A is distilled and deionized water (18 meg-ohm), sparged with helium while stirring for a minimum of 20 minutes, before installing under a blanket of helium, which is to be maintained regardless of whether the system is on or off.

Solvent B is 400 mM NaOH. Fill Solvent B bottle to mark with water and sparge with helium while stirring for 20 minutes. Add appropriate amount of 50% NaOH.

(50.0 g NaOH/100 g solution)*(1 mol NaOH/40.0 g NaOH)*(1.53 g solution/1 mL solution)*(1000 mL solution/1 L solution)=19.1 M NaOH in the container of 50/50 w/w NaOH.

0.400 M NaOH*(1000 mL $H_2O$/19.1 M NaOH)=20.8 mL NaOH

Round 20.8 mL down for convenience:

19.1M*(20.0 mL×mL)=0.400 M NaOH×mL=956 mL

Solvent D is 200 mM sodium acetate. Using 18 meg-ohm water, add approximately 450 mL deionized water to the Dionex sodium acetate container. Replace the top and shake until the contents are completely dissolved. Transfer the sodium acetate solution to a 1-L volumetric flask. Rinse the 500-mL sodium acetate container with approximately 100 mL water, transferring the rinse water into the volumetric flask. Repeat rinse twice. After the rinse, fill the contents of the volumetric flask to the 1-L mark with water. Thoroughly mix the eluent solution. Measure 360±10 mL into a 2-L graduated cylinder. Bring to 1800±10 mL. Filter this into a 2000-mL sidearm flask using the Millipore filtration apparatus with a 0.45 pm, Type HA membrane. Add this to the solvent D bottle and spurge with helium while stirring for 20 minutes.

The post column addition solvent is 300 mM NaOH. This is added postcolumn to enable the detection of sugars as anions at pH>12.3. Transfer 15±0.5 mL of 50% NaOH to a graduated cylinder and bring to 960±10 mL in water.

(50.0 g NaOH/100 g Solution)*(1 mol NaOH/40.0 g NaOH)*(1.53 g Solution/1 mL Solution)(1000 mL Solution/1 L solution)=19.1 M NaOH in the container of 50/50 w/w NaOH.

0.300 M NaOH*(1000 ml H2O/19.1 M NaOH)=15.7 mL NaOH

Round 15.7 mL down:

19.1 M*(15.0 mL/×mL)=0.300 M NaOH×mL=956 mL (Round 956 mL to 960 mL. As the pH value in the area of 0.300 M NaOH is steady, an exact 956 mL of water is not necessary.)

Set up the AS 50 schedule.

Injection volume is 5 uL for all samples, injection type is "Full", cut volume is 10 uL, syringe speed is 3, all samples and standards are of Sample Type "Sample". Weight and Int. Std. values are all set equal to 1.

Run the five standards at the beginning of the run.

After the last sample is run, run the mid-level standard again as a continuing calibration verification Run the control sample at any sample spot between the beginning and ending standard runs.

Run the samples.
Calculations
Calculations for Weight Percent of the Pulp Sugars $$\text{Normalized area for sugar} = \frac{(\text{Area sugar}) * (\mu g/mL \text{ fucose})}{(\text{Area Fucose})}$$

$$IS \text{ Corrected sugar amount}(\mu g/mL = \frac{((\text{Normalized area for sugar}) - (\text{intercept}))}{(\text{slope})}$$

$$\text{Monomer Sugar Weight}\% = \frac{IS - \text{Corrected sugar amt}(\mu g/mL)}{\text{Sample wt. (mg)}}$$

Example for arabinose:

$$\text{Monomer Sugar Weight}\% = \frac{0.15 \; \mu g/mL \text{ arabinose}}{70.71 \text{ mg arabinose}} * 20$$

$$= 0.043\%$$

Polymer Weight %=(Weight % of Sample sugar)*(0.88)

Example for Arabinan:

Polymer Sugar Weight %=(0.043 wt %)*(0.88)=0.038 Weight

Note: Xylose and arabinose amounts are corrected by 88% and fucose, galactose, rhamnose, glucose, and mannose are corrected by 90%.

The results are reported as percent sugars on an oven-dried basis.

In order to evaluate the nonwoven meltblown lyocell fiber webs as distribution/storage cores, individual webs were converted into absorbent structures with at least two webs with superabsorbent polymer intermediate the two webs. Other nonwoven meltblown lyocell fiber webs were converted into absorbent structures with three or more webs with superabsorbent intermediate at least two webs. The resulting absorbent structures were used as distribution/storage cores as replacement for the storage core in Equate feminine hygiene pads manufactured by Tyco. The procedure for forming various core structures follows.

Forming Procedure from Nonwoven Meltblown Lyocell Fiber Webs

Sample A

Never dried nonwoven meltblown lyocell fiber webs, 52-5, were made and 0.3 g superabsorbent applied uniformly over the surface of the first web within approximately 5 mm of the edge. The second never dried web of the same dimension was laid over the first web with the superabsorbent and shims, (177 mm×11 mm×6 mm steel bars) were placed around the perimeter of the composite two web structure and pressed for 5 seconds at 10,000 prig (703 kg/cm$^2$). The samples were dried under restraint between belts in a drum dryer at 105° C. for 5 minutes. FIG. 3 is a cross section representative of this web structure after drying. This sample is represented in Tables 2 and 3.

Samples B and C

Dried nonwoven meltblown lyocell fiber webs, 59-2, were cut to a dimension of 19 cm×6 cm. BASF Hi-sorb 8600 superabsorbent polymer, from BASF Ludwigshafen, Germany. 0.3 g, superabsorbent was uniformly distributed over one web within approximately 5 mm of the edge.

In one case, Sample B, the perimeter of the web was wetted with water.

In another case, Sample C, 1% by weight carboxymethyl cellulose solution was applied to the perimeter of the web and covered with another web of the same dimension. Shims (177 mm×11 mm×6 mm steel bars) were then placed around the perimeter of the composite two web structure and pressed for 5 seconds at 10,000 psig (703 kg/cm$^2$). The samples were dried under restraint between belts in a drum dryer at 105° C. for 5 minutes. FIG. 3 is a cross section representative of these web structures after drying. These samples are represented in Tables 2 and 3.

Sample D

Never dried nonwoven meltblown lyocell fiber webs, 52-5, were made and 0.3 g superabsorbent applied uniformly over the surface of the first web within approximately 5 mm of the edge. The second never dried web of the same dimension was laid over the first web with the superabsorbent and pressed for 5 seconds at 10,000 psig (703 kg/cm$^2$). The samples were dried under restraint between belts in a drum dryer at 105° C. for 5 minutes. This sample is represented in Tables 2 and 3.

Example E 0.3 g of superabsorbent can be uniformly applied to one dry nonwoven meltblown lyocell fiber web, 59-2, within approximately 5 mm of the edge, sprayed uniformly with water and covered with the other dry web of the same sample and dimension. Pressing without shims and drying can be conducted as described in Sample D.

Sample F

Never dried nonwoven meltblown lyocell fiber webs, 52-5, were made and the second never dried web of the same dimension was laid over the first web and roll pressed for 5 seconds at 70 psig. The samples were drum dried under restraint between belts in a drum dryer at 105° C. for 5 minutes. The caliper of the combined webs was 0.07 mm and the basis weight was 80 g/m$^2$.

The liquid distribution and rewet properties of the resulting structures made with the nonwoven meltblown lyocell fiber webs were evaluated by replacement of the core material only in Equate feminine hygiene pads with the nonwoven structures of the present application. The Equate control pad has a nonwoven topsheet, a core material of a mixture of 9.6 g fluff pulp and 0.3 g superabsorbent polymer and a polyethylene backsheet. A tack strip on the exterior of the polyethylene backsheet secures the product to an undergarment.

Liquid Distribution/Rewet Test

Synthetic menstrual fluid was obtained from Courtray Consulting Labservice, 2, Charles MONSARRAT 59500 Douai, France. Twenty ml of the fluid was dispensed at a rate of 20 ml f 60 min. on the center of the pad through a stainless steel dosing ring, 8.5 cm×2.5 cm ID, 195 g. Liquid distribution and rewet performance was measured on the total length of the pad which was equally divided into three sections. Each section was about 6.7 to 7.3 cm long depending on shrinkage. Each of the three sections was weighed to determine the actual weight after subtraction of the dry weight to determine the amount of liquid in each section. Rewet was measured 20 minutes after the conclusion of the test. In the test, Whatman filter paper, catalogue number 1003-917, was cut to 6 cm×22 cm and ten sheets placed in the middle of each of the sections. A rectangular weight, 6 cm×22, 4600 g weight (14 kPa/2 psi) was placed on the filter paper stack for five minutes. Rewet was calculated by subtracting the dry weight from the final weight of the filter paper.

The results of testing various absorbent structures that have meltblown lyocell fiber nonwoven webs are given in Tables 2-5, Table 6 gives the properties of Samples A through D and the Equate control sample.

Liquid distribution for all meltblown lyocell fiber nonwoven webs is significantly better than the Equate control sample. For example, Sample A, Table 2, made from two never dried nonwoven meltblown fiber webs with superabsorbent polymer intermediate the two webs had 4.93 g and 4.67 g of liquid at each end, each end representing one-third of the total structure length while the Equate product only had 0.27 and 0.53 g liquid in the corresponding areas. Similarly, sample A* in Table 4 made from two never dried webs of the nonwoven meltblown lyocell fiber webs, an intermediate layer with superabsorbent polymer and another two webs had 5.9 g liquid on one end and 4.34 g on the other end. The Equate control only had 0.2 and 0.41 g. in the corresponding areas.

Rewet performance of the absorbent web structures is approximately equal for samples A-D but lower than the Equate control, Table 3. Rewet can be improved by the addition of additional webs, for example, with three nonwoven meltblown lyocell fiber webs made from never-dried webs, superabsorbent and then an additional three webs, the rewet is lower than structures made from two webs with superabsorbent between the second and third web, Table 5.

Absorbent structures of the present application are thin. Sample A*, Tables 4-6, made from never-dried nonwoven meltblown lyocell fiber webs (two webs with superabsorbent polymer intermediate the webs), has a thickness of 2.45 mm while the Equate core sample has a 12 mm thickness. The densities are 0.89 and 0.051, respectively and the fiber weight 2.34 and 9.9 respectfully. The dimensions of the core were 20×5.5 cm and 21.5×21.75, respectively. The structures also have high web integrity. Absorbent cores in the present application cannot be broken in the integrity test under wet or dry conditions described in U.S. Pat. No. 5,877,09. Nonwoven meltblown lyocell fiber webs with superabsorbent polymer intermediate two webs have a dry and wet integrity of greater than 7 Newtons and 5 Newtons, respectively. Equate samples ranged from 2.4 to 6.7 Newtons, dry, with an average of 4.5 Newtons, and 1.3 to 2.3 Newtons, wet, with an average of 1.9 Newtons.

TABLE 2

Liquid Distribution Of Meltblown Lyocell Fiber Nonwoven Webs Jan. 17, 2008

| | Sample No. | | | | | | |
|---|---|---|---|---|---|---|---|
| | A | B | C | D | Equate | Equate (1) | Equate (2) |
| Total, g | 19.43 | 19.35 | 19.33 | 19.71 | 19.20 | 20.05 | 19.33 |
| End, g | 4.93 | 4.09 | 4.29 | 4.84 | 0.27 | 3.30 | 2.41 |
| Middle, g | 9.83 | 10.30 | 9.99 | 9.59 | 18.39 | 13.11 | 13.97 |
| End, g | 4.67 | 4.95 | 5.05 | 5.29 | 0.53 | 3.64 | 2.95 |

(1) Equate core was replaced with two webs 46-4/0.3 g superabsorbent/two webs 46-4
(2) Equate core was replaced with three webs 46-4/0.3 g superabsorbent/three webs 46-4

TABLE 3

Rewet Performance Of Meltblown Lyocell Fiber Nonwoven Webs Jan. 17, 2008

| | Sample No. | | | | | | |
|---|---|---|---|---|---|---|---|
| | A | B | C | D | Equate | Equate (1) | Equate (2) |
| End, g | 2.26 | 3.03 | 2.96 | 2.72 | 0.01 | 0.58 | 0.28 |
| Middle, g | 4.65 | 4.28 | 4.32 | 4.17 | 2.07 | 3.00 | 2.35 |
| End, g | 2.59 | 2.38 | 2.08 | 2.58 | 0.00 | 0.36 | 0.10 |
| Total Rewet, g | 9.50 | 9.69 | 9.37 | 9.47 | 2.08 | 3.94 | 2.72 |

(1) Equate core was replaced with two webs 46-4/0.3 g superabsorbent/two webs 46-4
(2) Equate core was replaced with three webs 46-4/0.3 g superabsorbent/three webs 46-4

TABLE 4

Liquid Distribution of Meltblown Lyocell Fiber Nonwoven Webs Feb. 22, 2008

| | Sample No. | | | | |
|---|---|---|---|---|---|
| | A* | A** | B* | B** | Equate |
| Total, g | 19.79 | 19.61 | 19.81 | 19.53 | 20.05 |
| End, g | 5.90 | 5.21 | 6.07 | 5.76 | 0.02 |

TABLE 4-continued

Liquid Distribution of Meltblown Lyocell Fiber Nonwoven Webs
Feb. 22, 2008

| | Sample No. | | | | |
|---|---|---|---|---|---|
| | A* | A** | B* | B** | Equate |
| Middle, g | 9.55 | 10.13 | 7.90 | 8.05 | 19.61 |
| End, g | 4.34 | 4.28 | 5.84 | 5.72 | 0.41 |

A* - two never dried nonwoven meltblown lyocell webs, 0.3 g SAP, two never dried nonwoven meltblown lyocell webs, pressed with shims at edge, dried under restraint.
A** - three never dried nonwoven meltblown lyocell webs, 0.3 g SAP, three never dried nonwoven meltblown lyocell webs, pressed with shims at edge, dried under restraint.
B* - two nonwoven meltblown lyocell webs, 0.3 g SAP, twononwoven meltblown lyocell webs, edges wetted with water, pressed with shims at edge, dried under restraint.
B** - three nonwoven meltblown lyocell webs, 0.3 g SAP, three nonwoven meltblown lyocell webs edges wetted with water, pressed with shims at edge, dried under restraint.

TABLE 5

Rewet Performance of Meltblown Lyocell Fiber Nonwoven Webs

| | Sample No. | | | | |
|---|---|---|---|---|---|
| | A* | A** | B* | B** | Equate |
| End, g | 2.49 | 1.36 | 3.74 | 2.70 | 0.00 |
| Middle, g | 4.79 | 3.87 | 4.70 | 3.65 | 1.06 |
| End, g | 2.78 | 1.79 | 3.03 | 1.88 | 0.00 |
| Total Rewet, g | 10.06 | 7.02 | 11.47 | 8.22 | 1.06 |

A* - two never dried nonwoven meltblown lyocell webs, 0.3 g SAP, two never dried nonwoven meltblown lyocell webs, pressed with shims at edge, dried under restraint.
A** - three never dried nonwoven meltblown lyocell webs, 0.3 g SAP, three never dried nonwoven meltblown lyocell webs, pressed with shims at edge, dried under restraint.
B* - two nonwoven meltblown lyocell webs, 0.3 g SAP, two nonwoven meltblown lyocell webs, edges wetted with water, pressed with shims at edge, dried under restraint.
B** - three nonwoven meltblown lyocell webs, 0.3 g SAP, three nonwoven meltblown lyocell webs, edges wetted with water, pressed with shims at edge, dried under restraint.

TABLE 6

Meltblown Lyocell Fiber Nonwoven Web Characteristics

| Sample | Core dimension L × W, cm | Thickness, mm | Density, g/cm³ | Weight, g |
|---|---|---|---|---|
| A* | 20 × 5.5 | 2.45 | 0.089 | 2.34 |
| A** | 20 × 5.5 | 3.5 | 0.083 | 3.39 |
| B* | 21.5 × 6.0 | 1.4 | 0.114 | 2.25 |
| B** | 22.0 × 7.0 | 1.7 | 0.115 | 3.19 |
| Equate, whole core | 21.5 × 7.5 | 12.0 | 0.051 | 9.9 |

A* - two I never dried nonwoven meltblown lyocell webs, 0.3 g SAP, two never dried nonwoven meltblown lyocell webs, pressed with shims at edge, dried under restraint.
A** - three I never dried nonwoven meltblown lyocell webs, 0.3 g SAP, three never dried nonwoven meltblown lyocell webs, pressed with shims at edge, dried under restraint.
B* - two nonwoven meltblown lyocell webs, 0.3 g SAP, twononwoven meltblown lyocell webs, edges wetted with water, pressed with shims at edge, dried under restraint.
B** - three nonwoven meltblown lyocell webs, 0.3 g SAP, three nonwoven meltblown lyocell webs, edges wetted with water, pressed with shims at edge, dried under restraint.

The nonwoven webs in the present application are suitable for use in absorbent structures such as feminine hygiene products and disposable diapers. The nonwoven webs can be used alone or in combination with other structures such as acquisition and/or distribution layers or with storage cores.

The invention claimed is:

1. An absorbent structure comprising:
   at least one first nonwoven meltblown lyocell fiber web;
   at least one second nonwoven meltblown lyocell fiber web;
   said first and second nonwoven meltblown lyocell fiber webs each having an upper surface, a lower surface, longitudinal edges and width edges;
   a superabsorbent polymer intermediate said lower surface of said first web and the upper surface of said second web; and
   wherein said absorbent structure has first thickness; and
   wherein said first and second web are conterminous,
   the longitudinal edges and the width edges have a second thickness less than the first thickness, and
   the perimeters of the lyocell webs are bonded together
   wherein the superabsorbent polymer is the only material between the first and second webs within the bonded perimeters.

2. The absorbent structure of claim 1 wherein said lyocell fibers have a diameter of from 3 microns to 20 microns.

3. The absorbent structure of claim 1 wherein said lyocell fibers have a diameter of from 5 microns to 15 microns.

4. The absorbent structure of claim 1 wherein the basis weight of the webs are the same.

5. The absorbent structure of claim 1 wherein the basis weight of the webs are different.

6. The absorbent structure of claim 1 wherein the basis weight of the first web is from 5 g/m² to 150 g/m² and the second web is from 5 g/m² to 150 g/m².

7. The absorbent structure of claim 1 comprising at least three nonwoven meltblown lyocell fiber webs; and
   wherein the superabsorbent is intermediate to two or more of said nonwoven meltblown lyocell fiber webs.

8. The absorbent structure of claim 1 comprising at least four nonwoven meltblown lyocell fiber webs; and
   wherein the superabsorbent is intermediate to two or more of said nonwoven meltblown lyocell fiber webs.

9. A method for making an absorbent structure comprising the steps of:
   providing at least one first nonwoven meltblown lyocell fiber web;
   providing at least one second nonwoven meltblown lyocell fiber web;
   said first and second nonwoven meltblown lyocell fiber webs each having an upper surface, a lower surface, longitudinal edges and width edges;
   providing a superabsorbent polymer intermediate said lower surface of said first nonwoven meltblown lyocell fiber web and the upper surface of said second nonwoven meltblown lyocell fiber web;
   wherein said first and second nonwoven meltblown lyocell webs are conterminous;
   wherein said absorbent structure comprising said first and said second nonwoven meltblown lyocell webs together have a first thickness;
   wherein said longitudinal and said width edges are compressed to a second thickness less than said first thickness, and
   wherein the perimeters of the lyocell webs are bonded together
   wherein the superabsorbent polymer is the only material between the first and second webs within the bonded perimeters.

10. The method of claim 9 wherein the first nowoven meltblown lyocell fiber web and the second nowoven meltblown lyocell fiber web have the same basis weight.

11. The method of claim 9 wherein the first nowoven meltblown lyocell fiber web and the second nowoven meltblown lyocell fiber web have a different basis weight.

12. The method of claim 9 wherein the meltblown lyocell fibers are from 3 to 20 microns in diameter.

13. The method of claim 9 wherein said longitudinal edges and said width edges of said nonwoven meltblown lyocell fiber webs contain a bonding agent.

14. The method of claim 10 wherein said longitudinal edges and said width edges further comprise an adhesive intermediate said first and said second nonwoven meltblown lyocell fiber web edges.

15. A method for making an absorbent structure comprising the steps of:
- providing at least one first never-dried nonwoven meltblown lyocell fiber web;
- providing at least one second never-dried nonwoven meltblown lyocell fiber web;
- said first and second never-dried nonwoven meltblown lyocell fiber webs each having an upper surface, a lower surface, longitudinal edges and width edges;
- providing a superabsorbent polymer intermediate said lower surface of said first never-dried fiber web and the upper surface of said second fiber web; and
- wherein said first and second never-dried nonwoven meltblown lyocell fiber webs are conterminous;
- wherein said absorbent structure comprising said first and second never-dried nonwoven meltblown lyocell fiber webs each have a first thickness;
- wherein said absorbent structure is compressed to a thickness less than said first thickness; and
- drying said never-dried nonwoven meltblown lyocell fiber webs
- wherein the superabsorbent polymer is the only material between the first and second webs within the edges.

16. The absorbent structure of claim 1 wherein a bonding agent or adhesive is also between the first and second webs.

17. The method of claim 9 wherein a bonding agent or adhesive is also between the first and second webs.

18. The method of claim 15 wherein a bonding agent or adhesive is also between the upper and lower webs.

* * * * *